United States Patent [19]

Ray et al.

[11] 4,020,079
[45] Apr. 26, 1977

[54] ANTI-INFLAMMATORY SYDNONES

[75] Inventors: Richard E. Ray, Morton Grove; Hans A. Wagner, Skokie, both of Ill.

[73] Assignee: G. D. Searle & Co., Chicago, Ill.

[22] Filed: Aug. 1, 1974

[21] Appl. No.: 493,930

[52] U.S. Cl. .................. 260/307 A; 260/514 R; 260/514 G; 260/514 H; 260/534 S; 260/563 D; 260/563 P; 260/583 EE; 424/272

[51] Int. Cl.$^2$ .................................. C07D 271/04

[58] Field of Search ........................ 260/307 A

[56] References Cited

UNITED STATES PATENTS 3,883,548  5/1975  Hill .................. 260/307 A

FOREIGN PATENTS OR APPLICATIONS 1,064,521  9/1959  Germany

OTHER PUBLICATIONS

Stewart–J. Org. Chem. 27, 687–688 (1962).

*Primary Examiner*—Raymond V. Rush
*Attorney, Agent, or Firm*—John A. Dhuey

[57] ABSTRACT

3-Alkylthioalkyl-4-optionally substituted sydnones, useful as anti-inflammatory pharmaceutical agents, are prepared.

4 Claims, No Drawings

ANTI-INFLAMMATORY SYDNONES

The present invention is concerned generally with compounds of the sydnone family. More particularly, it is concerned with compounds of the following structural formula

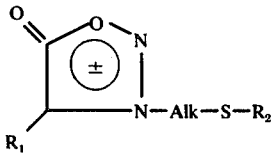

wherein $R_1$ is hydrogen, halogen, lower alkyl or cycloalkyl, $R_2$ is lower alkyl, cycloalkyl or adamantyl and Alk is lower alkylene.

Preferred among those compounds are the compounds in which $R_1$ is lower alkyl, $R_2$ is cycloalkyl or adamantyl and Alk is ethylene.

For the purposes of this invention, lower alkyl comprehends alkyl radicals, branched or straight-chain, having 1-7 carbon atoms inclusive, as illustrated by methyl, ethyl, propyl, isopropyl, butyl, tert-butyl and the like; cycloalkyl comprehends cycloalkyl radicals having 5-8 carbon atoms inclusive, as illustrated by cyclopentyl, cycloalkyl, cycloheptyl and cyclooctyl; and lower alkylene comprehends alkylene radicals, branched and straight-chain, having 1-7 carbon atoms inclusive, as illustrated by methylene, ethylene, propylene and the like. Halogen comprehends bromine, iodine, chlorine and fluorine.

The compounds of this invention are prepared by a sequence of steps beginning with the heating together of an amine of the formula

and a 2-bromoalkanoic acid of the formula

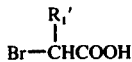

in the presence of sodium methoxide or potassium tert-butoxide, using tert-butyl alcohol as solvent, thereby producing the amino acid of the formula

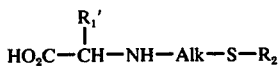

wherein $R_2$ and Alk are the same as defined above and $R_1'$ is hydrogen, lower alkyl or cycloalky. Contacting of that compound with sodium nitrite and an acid, e.g. hydrochloric acid, affords the corresponding N-nitroso derivative of the formula

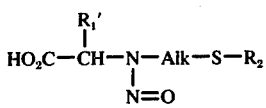

Prolonged contacting of the N-ntiroso derivatives with acetic anhydride affords the instant sydnones of the formula

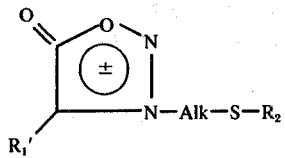

wherein $R_1'$, $R_2$ and Alk are as defined hereinbefore.

The preparation of the 4-halosydnones of the instant invention having the formula

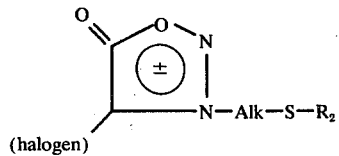

is accomplished by contacting the corresponding 4-unsubstituted sydnone, in the presence of potassium acetate, with halogen and acetic acid.

The compounds to which this invention relates are useful by reason of their valuable biological properties. An especially valuable property characteristic of the instant compounds in anti-inflammatory activity, which is evident from the results of a standardized test for this property described in the paragraph beginning with line 34 in column 2 of U.S. Pat. No. 3,528,966.

Further evidence of the anti-inflammatory utility of the instant compounds is provided by the results of a standardized test for their capacity to inhibit the edema induced in rats by injection of carrageenin. The procedure is a modification of one described by Winter et al., Proc. Soc. Exp. Biol. Med., 111, 544(1962). Compound is administered subcutaneously or intragastrically —dissolved or suspended in 0.5ml. of aqueous 0.85% sodium chloride, propylene glycol, a mixture of these vehicles, or corn oil —to each of 10 male rats weighing 100-130gm. A like group of rats to which is identically and concurrently administered vehicle alone serves as controls. Precisely 1 hour later, each animal is injected under the plantar surface of each hind foot with 0.1ml. of an aqueous 1% solution of carrageenin (Marine Colloids, Inc., Type 402). A compound is considered anti-inflammatory if the average total volume of the 2 hind feet in the group treated therewith, which is measured in arbitrary units 5 hr. after the carrageenin injection, is significantly ($P \leq 0.05$) less than the corresponding value for the control group.

Still further evidence of the anti-inflammatory utility of the instant compounds is provided by the results of a standardized test for their capacity in inhibit the edema induced in rats by injection of *Mycobacterium butyricum.* butyricum. The procedure, which is similar to one described by Pearson et at. in *Arthritis Rheumat.*, 2, 440 (1959), follows. Intact male Sprague-Dawley rats are randomized in groups of 12, 1 group for each compound to be tested plus 1 group to serve as controls. Each animal is injected intradermally (without any anesthesia on the base of the tail with 0.6mg. of dry heat-killed *Mycobacterium butyricum* (Difco 0640-33) suspended in 0.05ml. of paraffin oil contaning 2% digitonin, whereupon the prescribed dose of compound (initially 5mg.) —dissolved or suspended in a vehicle consisting of 0.2 ml. of either corn oil or a mixture of 20ml. of aqueous 0.85% sodium chloride with 1drop of polysorbate 80—is intragastrically or subcutaneously administered. Administration thus of compound is repeated daily for the next 18 consecutive days. The control group is identically and concurrently administrated vehicle alone. On the 20th day, the rats are sacrificed, and the total volumn of each pair of hind feet is measured in arbitrary units. A commpound is considered anti-inflammatory if the average volume of the hind feet in the group treated therewith is significantly ($P \leq 0.05$) less than the corresponding value for the control group.

The invention will appear more fully from the examples which follow. They are not to be construed as limiting the invention either in spirit or scope as variations in materials and methods will be apparent to those skilled in the art. In the examples which follow temperatures are given in degrees Centigrade (° C.) and quantities of materials are given in parts by weight unless otherwise specified.

EXAMPLE 1

To a solution containing 30 parts of sodium methoxide and 198parts of methanol, maintained at 25°under a nitrogen atmosphere, is added rapidly 39 parts of cyclohexyl mercaptan. 51 Parts of 2-bromoethylamine hydrobromide then is added portion wise while maintaining the temperature at 25–30°, and the reaction mixture is stirred for 30 minutes. Then the mixture is refluxed for 3 hours, and the solid which forms is separated by filtration and washed with methanol. Residual solvent is removed under reduced pressure to yield a solid which is diltuted with water and extracted with ether. The ethereal extracts are dried over a molecular sieve and filtered. The solvent is removed under reduced pressure to afford an oil which is dissolved in anhydrous ether. That solution is cooled in an ice bath while slowly adding isopropanolic hydrochloric acid. The precipitate which forms is recovered by filtration, washed with ether and air dried to afford pure 2-(cyclohexylthio)ethyl-amine hydrochloride, melting at about 210°–211°.

EXAMPLE 2

To a stirred solution of 22.4parts potassium tert-butoxide in 400 parts by volume of tert-butanol, under a nitrogen atomosphere, is added sucessively 19.62parts of 2-(cyclohexylthio)ethylamine hydrochloride and 15.3parts of 2-bromopropionic acid. The mixture is refluxed for 3 hours, then dried under reduced pressure. The material remaining is dissolved in 200 parts of water containing 10 parts of sodium hydroxide and extracted with ether. The aqueous solution is cooled in an ice bath and acidified to pH 5 with concentrated hydrochloric acid. The solid is collected by filtration and dried under reduced pressure to yield N-[2-(cyclohexyl-thio) ethyl]alanine.

EXAMPLE 3

The N-[2-(cyclohexylthio)ethyl]alanine prepared in Example 2 is suspended in 210 parts of acetic acid and that mixture is treated, over a period of 20 minutes, with a solution containing 7 parts of sodium nitrite and 70 parts of water. The resulting mixture is stirred for 1½ hours, then filtered. The filtrate is added to 2000 parts of water and extracted with methylene chloride. The organic phase is separated, washed with water, dried over anhydrous sodium sulfate, filtered and then evaporated to dryness under reduced pressure to afford, as an oil, N-[2-(cyclohexylthio)- ehtyl]-N-nitrosoalanine.

EXAMPLE 4

The oil obtained in Example 3, N-[2-(cyclohexyl-thio)ethyl]-N-nitrosoalanine, is treated with 54 parts of acetic anhydride and allowed to stand for 4 days at room temperature. After that time, the reaction mixture is added to 500 parts of water and extracted with methylene chloride. The organic extracts are washed with water and aqueous sodium bicarbonate, dried over anhydrous sodium sulfate and evaporated to dryness. The oil remaining is crystallized from ether by seeding and cooling. The crystalline material is recovered by filtration and dried to afford pure 3-[2-(cyclohexylthio)- ethyl]-4-methylsydnone, melting at about 82°–83°. That compound is represented structurally by the following formula

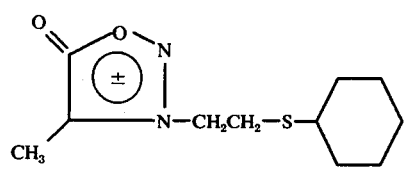

EXAMPLE 5

32.9Parts of 2-(1-adamantylthio)ethylamine, 17.95 parts of potassium tert-butoxide and 24.5parts of 2-bromopropionic acid are added, successively, to 236parts of tert-butanol and the mixture is stirred at reflux, under a nitrogen atmosphere, for 5 hours. The solvent is removed under reduced pressure and the residue is dissolved in 300 parts of water containing 12 parts of sodium hydroxide. Extraction with ether, followed by acidification of the aqueous extracts with acetic acid affords a solid, which is recovered by filtration, washed with water and dried. The product so obtained is N-[2-(1-adamantylthio)ethyl]alanine, melting at about 229°–232°

EXAMPLE 6 a stirred solution of 22.7parts of N-[2-(1- adamantyl-thio)ethyl]alanine in 216 parts of acetic acid is cooled to 15°, then treated with a solution of 6.2 parts of sodium nitrite in 20 parts of water, added dropwise over a is minute period. Stirring is continued at low temperature for an additional 15 minutes, then at room temperature for another 15 minutes. The resultant clear yellow solution is added to 1000 parts of ice-water and stirring is continued. The resultant mixture is extracted with methylene chloride. The organic phase is separated, washed with water, dried over anhydrous sodium sulfate and evaporated to dryness to yield, as a gum-like material, N-[2-(1-adamantylthio)ethyl]-N-nitroso-alanine.

EXAMPLE 7

The N-[2-(1-adamantylthio)ethyl]-N-nitroso- alanine prepared in Example 6 is dissolved in 163 parts of acetic anhydride, then allowed to stand at room temperaturefor 24 hours. The solution is heated briefly to 64°on a steam bath and allowed to cool to room temperature. Then the solution is added to 1000 parts of water and stirred for 3 hours. The solid which forms is collected by filtration, washed successively with water, and saturated sodium bicarbonate and water, and dried. Recrystallization of the solid from methylene chloride-ether affords pure 3-[2-(1-adamantylthio)ehtyl]- 4-methylsydnone, melting at about 92°–93°and represented by the following structural formula

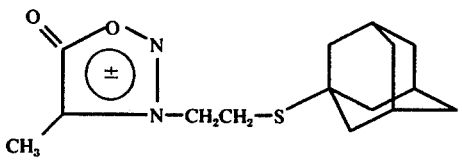

EXAMPLE 8

A mixture of 42.3 parts of 2-(1-adamantylthio)- ethylamine, 10.8 parts of sodium methoxide, 39.0parts of 2-bromo-2-tert-butyl acetic acid and 315parts of tert-butanol is refluxed, under a nitrogen atmosphere, for 5 hours. The product is recovered in the manner described in Example 5 to yield 2-tert-butyl-N-[2-(1-adamantylthio)ethyl]glycine, melting at about 220°–230°.

EXAMPLE 9

32.5 Parts of the 2-tert-butyl-N-[2(1- adamantylthio)ethyl]glycine prepared in Example 8 is dissolved in 263 parts of acetic acid, then cooled to 15°and treated over a period of 15 minutes with a solution consisting of 8 parts of sodium nitrite and 30 parts of water. The resulting solution is cooled in an ice bath and stirred for 1 hour. The product is recovered in the manner described in Example 6to yield, as an oil, 2-tert-butyl-N-[2-(1-adamantylthio(ethyl]-N- nitrosoglycine.

EXAMPLE 10

The 2-tert-butyl-N-[2-(1adamantylthio)ethyl- N-nitrosoglycine prepared in Example 9 is added to 216 parts of acetic anhydride. That mixture is stirred for about 16 hours, then heated on a steam bath and kept at 85°for 15minutes. After allowing the reaction mixture to cool to about room temperature, the mixture is added to water and extracted with methylene chloride. The organic extracts are washed with aqueous sodium bicarbonate and water and dried over anhydrous sodium sulfate. Methylene chloride is removed under reduced pressure and ether added, followed by n-pentane. That mixture is allowed to stand in a dry-ice bath for approximately 16 hours, thereby inducing crystallization. The crystalline material is recovered by filtration and washed with a 1:1 ether-pentane solution. Upon drying there is afforded pure 3-[2-(1-adamantylthio)ethyl]-4-tert-butyl- sydnone, melting at about 55°–56°That compound is represented by the following structural formula

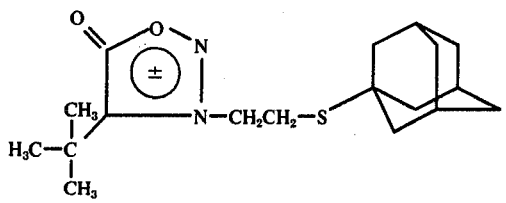

EXAMPLE 11

By substituting an equivalent quantity of tert-butyl mercaptan in the procedure of Example 1, and subsequently following the procedures outlined in Examples 1, 2, 3 and 4, there is obtained 3-[2-(tert-butylthio)-ethyl]-4-methylsydnone.

EXAMPLE 12

By substituting an equivalent quantity of ethyl mercaptan in the procedure of Example 1, and subsequently following the procedures of Examples 1, 2, 3 and 4, there is obtained 3-[2-(ethylthio)ethyl]-4- methysydnone.

EXAMPLE 13

Substitution of an equivalent quantity of 2-brommobutyric acid in the procedure of Example 2 affords N-[2-(cyclohexylthio)ethyl]-2-ethylglycine. That compound is processed according to the procedures outlined in Examples 3 and 4 to yield 3[2-(cyclohexyltio)ehtyl]-4-ethylsydnone.

EXAMPLE 14

Substitution of an equivalent quantity of cyclopentyl mercaptan in the procedure of Example 1, and subsequently following the procedures outlined in Examples 2, 3 and 4, affords 3-[2-(cyclopentylthio)- ethyl]-4-methylsydnone.

EXAMPLE 15

By substituting an equivalent quantity of bromoacetic acid in the procedure of Example 2, and subsequently following the procedures of Examples 3 and 4, there is obtained 3-[2-(cyclohexylthio)ethyl]- sydnone.

EXAMPLE 16

4 Parts of 3-[2-(cyclohexylthio)ethyl]sydnone is stirred with 4 parts of potassium acetate in 40 parts by volumn of acetic acid while 2.8 parts of bromine in 10 parts by volume of acetic acid is added dropwise. Stirring is continued for 30 minutes and then the reaction mixture is poured into water, filtered and washed with water to give 3-[2-(cyclohexylthio)ethyl]-4-bromosydnone.

What is claimed is:
1. A compound of the formula

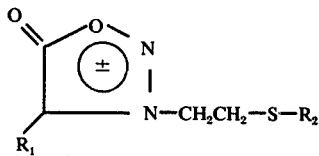

wherein $R_1$is lower alkyl having 1–7carbon atoms inclusive and $R_2$is cycloalkyl having 5–8carbon atoms inclusive or adamantyl.

2. As in claim 1, the compound which is 3- [2-(cyclohexythio)ethyl]-4-methylsydnone.

3. As in claim 1, the compound which is 3- [2-(adamantylthio)ethyl]-4-methylsydnone.

4. As in claim 1, the compound which is 3- [2-(1-adamantylthio)ethyl]-4-tert-butyl sydnone.

* * * * *